(12) United States Patent
Smedinga et al.

(10) Patent No.: US 10,561,855 B2
(45) Date of Patent: Feb. 18, 2020

(54) LIGHTING DEVICE AND METHOD FOR MASKING AN EDGE TRANSITION

(71) Applicant: SIGNIFY HOLDING B.V., Eindhoven (NL)

(72) Inventors: Oege Smedinga, Eindhoven (NL); Georg Hagenauer, Eindhoven (NL); Ype Bernardus Brada, Eindhoven (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 360 days.

(21) Appl. No.: 15/323,961

(22) PCT Filed: Jul. 6, 2015

(86) PCT No.: PCT/EP2015/065393
§ 371 (c)(1),
(2) Date: Jan. 4, 2017

(87) PCT Pub. No.: WO2016/005339
PCT Pub. Date: Jan. 14, 2016

(65) Prior Publication Data
US 2017/0157420 A1  Jun. 8, 2017

(30) Foreign Application Priority Data
Jul. 8, 2014  (EP) .................................... 14176100

(51) Int. Cl.
*F21V 8/00* (2006.01)
*A61N 5/06* (2006.01)
(52) U.S. Cl.
CPC ........... *A61N 5/0618* (2013.01); *G02B 6/005* (2013.01); *G02B 6/0036* (2013.01);
(Continued)

(58) Field of Classification Search
CPC .......... A61N 5/0618; A61N 2005/0643; A61N 2005/0663; A61N 2005/0667;
(Continued)

(56) References Cited

U.S. PATENT DOCUMENTS

| 2010/0165241 A1 | 7/2010 | Kim et al. |
| 2013/0105299 A1 | 5/2013 | Kim |
| 2014/0043850 A1* | 2/2014 | Thompson ........... G02B 6/0035 362/607 |

FOREIGN PATENT DOCUMENTS

| CN | 202024194 U | 11/2011 |
| JP | 08122778 A | 5/1996 |

(Continued)

*Primary Examiner* — Aaron F Roane
(74) *Attorney, Agent, or Firm* — Daniel J. Piotrowski (57) ABSTRACT

The present disclosure concerns a lighting device (100) and a method of masking an edge transition (15e). An edge structure (15) provides the light with a first edge transition (L1) along a circumference (15e) of the edge structure (15). A patterned layer (11) is provided between the edge structure (15) and the front side (31) of the device. The patterned layer (11) comprises a gradient edge pattern (11g) configured to provide the transmitted light with a second edge transition (L2). The gradient edge pattern (11g) is configured with respect to the circumference (15e) of the edge structure (15) to smoothen the first edge transition (L1). A diffuser (10) is disposed between the front side (31) and the patterned layer (11) for scattering the light of the second edge transition (L2) to smoothen the second edge transition (L2) of the gradient edge pattern (11g).

14 Claims, 9 Drawing Sheets

(52) U.S. Cl.
CPC ......... *G02B 6/0051* (2013.01); *G02B 6/0055* (2013.01); *G02B 6/0085* (2013.01); *A61N 2005/0643* (2013.01); *A61N 2005/0663* (2013.01)

(58) Field of Classification Search
CPC .... G02B 5/021; G02B 5/0278; G02B 6/0036; G02B 6/005; G02B 6/0051; G02B 6/0055; G02B 6/0085; G02B 27/0018; G02B 6/0058
USPC .......................................................... 607/90
See application file for complete search history.

(56) References Cited

FOREIGN PATENT DOCUMENTS

| | | | |
|---|---|---|---|
| JP | 2000276921 A | 10/2000 |
| JP | 2002022908 A | 1/2002 |
| JP | 2002214407 A | 7/2002 |
| JP | 2004029220 A | 1/2004 |
| JP | 2014150049 A | 8/2014 |
| KR | 2008090681 A | 10/2008 |
| WO | 201117114 A1 | 10/2010 |

\* cited by examiner

LIGHTING DEVICE AND METHOD FOR MASKING AN EDGE TRANSITION

CROSS-REFERENCE TO PRIOR APPLICATIONS

This application is the U.S. National Phase application under 35 U.S.C. § 371 of International Application No. PCT/EP2015/065393, filed on Jul. 6, 2015, which claims the benefit of European Patent Application No. 14176100.7, filed on Jul. 8, 2014. These applications are hereby incorporated by reference herein.

TECHNICAL FIELD AND BACKGROUND

The present disclosure relates to a lighting device such as a light therapy device. The disclosure further relates to a method of masking an edge transition of transmitted light behind the circumference of an edge structure in a lighting device.

Light therapy consists of the exposure of a subject to a prescribed dosage of light. For example, light having a particular frequency may be used to treat circadian rhythm disorders. For the light therapy device to be effective, it typically needs a relatively high light output. To prevent blinding (or to improve eye comfort), the light can be distributed over a relatively large surface of the device, e.g. using a light guide plate. However, especially when operating at a high light output, any edges of components in the device, including an edge of the light guide, may cast an edge transition (shadow) on the light emitted from the device. Such shadows and sharp edge transitions may cause a user to experience ghost (after) images in his retina. Accordingly, to improve eye comfort it is desired to provide a gradient light source, i.e. masking a sharp transition between the bright display and a first area having a relatively low transparency.

To mask an edge transition, a gradient pattern at an exit surface of the lighting device can be used to provide a transition from light to dark at an edge of the display surface. For example, WO2010117114 describes a display apparatus including a display module, a front panel provided in front of the display module, and a pattern which is formed over the front panel. One portion of the pattern that is closer to an edge of the front panel allows less transmittance of light than other portions of the pattern. However, to provide a smooth edge transition for a very bright light source, the pattern needs to extend over a considerable distance, which may lead to deterioration of the total light output of the device.

Accordingly, it is desired to improve the masking of an edge transition of a light output window with minimal sacrifice to its light output efficiency.

SUMMARY

A first aspect of the present disclosure provides a lighting device comprising a light source configured to generate light. The lighting device comprises a front side configured to emit the light from the lighting device. The lighting device comprises an edge structure forming an outer circumference of a light window through which the light is transmitted towards the front side. The edge structure, in use, provides the transmitted light with a first edge transition on the emitted light along the circumference of the edge structure. The first edge transition can be a relatively sharp transition, e.g. providing a relatively high contrast at the edge of the light window. The lighting device comprises a patterned layer comprising a gradient edge pattern configured to provide the transmitted light with a second edge transition. The gradient edge pattern is arranged with respect to the circumference of the edge structure to superimpose the second edge transition on the first edge transition The second edge transition can be a relatively smooth transition, e.g. providing a lower contrast at the edge than the first edge transition. The lighting device comprises a diffuser disposed between the front side and the patterned layer. The diffuser is configured for scattering the light of the second edge transition to provide the light emitted from the front side with a third edge transition. The diffuser can help to smoothen and/or mask the second edge transition of the gradient edge pattern by scattering the light.

By means of the gradient pattern, the luminosity of transmitted light is varied from dark to light to provide partial masking of the edge. By means of the diffuser, the light with a gradient luminosity is directionally scattered with minimal sacrifice to the light output efficiency. By means of combined luminosity variation and directional scattering, the edge transition is found to be more gradual than expected based on the individual effects of the gradient pattern or diffuser.

To provide an edge transition, the patterned layer may be configured to transmit the light at different luminosities over the gradient edge pattern. Preferably, the patterned layer comprises a first area having a relatively low transparency and a second area having a relatively high transparency, wherein the gradient edge pattern is configured to provide a luminosity transition gradient of the transmitted light extending between the first area and the second area. For example, it is found preferable that the luminosity through the first area having the relatively low transparency of the layer is less than 30% of the full luminosity present at the second area, preferably less than 20%, more preferably less than 10%, or even 0% of the full luminosity, i.e. the light is fully blocked at a first area having the relatively low transparency of the gradient edge. By providing the gradient edge over a minimum width, a smooth transition can be achieved. On the other hand, when the gradient edge is too wide it may deteriorate efficiency. Such a wide edge is not needed due to the effect of the diffuser. Accordingly, it is found advantageous to provide a gradient edge having a width in the range of 2 to 20 millimetres, preferably 3 to 15 millimetres. To provide sufficient alteration of the transmitted light, especially in parts where most light should be blocked, the patterned layer may comprise a first material to absorb and/or reflect a large percentage of the light, e.g. at least 80%, at least 90%, at least 95%, at least 99% or even more. On the other hand, a second material forming the gradient edge can be a different material that can have a lower absorption/reflection. To mask the material of the patterned layer, the second material may have a colour matching that of the front side of the lighting device. For example, the first material can be black to provide maximum absorption, and the second material, facing the front side, can be white matching a white front side of the device. A gradient edge pattern may e.g. comprise a distribution of reflecting and/or translucent and/or absorbing figures. By varying density and/or size of the figures across the pattern, the amount of transmission per unit surface can be varied. One way to produce a patterned layer would be to print a pattern on to a transparent foil. By printing the pattern on a backside of the foil, opposite the frontside of the lighting device, the appearance of the pattern from the front side can be more shiny and smooth.

Diffusion or scattering is a process by which the spatial distribution of a beam of radiation is changed. One way to quantify diffusion is to use the ratio of diffuse transmission to total transmission. The ratio, also known as "haze" or "haze ratio" can e.g. be expressed as a percentage. For example, a perfectly clear (non-scattering) window can have a haze ratio of 0% while a perfect (Lambertian) diffusor can have a haze ratio of 100%. To provide sufficient masking of the edge transition as well as the gradient pattern, it is found desirable to configure the diffuser so as to provide a haze ratio of at least 10%, preferably at least 25%, more preferably at least 40%. It is noted that a 100% diffuser may cause a theoretically perfectly even surface with Lambertian transmittance, i.e. completely isotropic luminance. However, in a light therapy device a completely isotropic luminosity would not be effective because the light needs to be directed towards the user while the light travelling in other directions can be considered wasted. Accordingly, preferably, the haze is preferably at most 80%, more preferably at most 60%, for example 50%. By integrating the diffuser to form the frontside of the lighting device, a more compact device can be obtained.

Alternatively, or in addition, to improve the edge transition, the diffuser can spread the angular distribution of transmitted light. One way to quantify the spread would be to measure the étendue of the light with and without the diffuser. The étendue may for example be approximated as a product of the surface and the solid angle of the radiation. To provide sufficient spread of the light, it is found desirable to configure the diffuser so as to provide an increase in étendue by at least 5%, preferably at least 10%, more preferably at least 20%. It is noted that a complete diffuser may cause a theoretically perfectly white surface with Lambertian transmittance, i.e. completely isotropic luminance. However, in a light therapy device a completely isotropic luminosity would not be effective because the light needs to be directed towards the user. Accordingly, preferably, the increase in étendue is preferably at most 100% (i.e. a doubling of the solid angle over which the light is transmitted), more preferably at most 50%. By integrating the diffuser to form the frontside of the lighting device, a more compact device can be achieved.

By providing a spacing between the diffuser and the patterned layer, the edge transition can be even further improved (setback). In addition, a larger spacing is found to mask also details of the gradient pattern itself. This allows a relatively coarse pattern to be used while maintaining the smooth transition. By allowing a coarse pattern, the manufacture of the patterned layer can be simplified. To provide a desired effect, it is found preferable to have a spacing of at least 0.5 millimetre between the patterned layer and the diffuser, more preferably at least 1.0 millimetre, even more preferably at least 1.5 millimetre. On the other hand, too large a distance may completely negate the transition of the gradient pattern. Accordingly, it is found preferable to have a spacing of at most 5 centimetres, more preferably at most 2 centimetres, even more preferably at most 1 centimetre, for example between 1.9 and 4.5 mm.

For example, a light guide plate can be used to evenly spread light over a surface. Typically, the light guide plate is configured to emit the light from the light source towards the front side of the lighting device. To inject light into the plate, the light source can be placed at an edge of the plate, perpendicularly to the front face of the plate. To improve effective light transmission to a user, so-called brightness enhancement foil can be used. The brightness enhancement foil has a ridged structure to collimate transmitted light in a defined direction. In order to have a maximum gain in illuminance at the centre of the device, 2 brightness enhancement foils are arranged in such a way that the foils are collimated perpendicularly to each other. In practice, the arrangement is applied, in one foil, in the horizontal direction and, in the other foil, in the vertical direction. However, it is found that the ridged structure of the foil can cause visible elongated light spots, further called "light lanes", at the edge of the foil where the light source is located. This can adversely affect the present purpose of masking the edge transition. To counteract the formation of light lanes while still maximizing the collimating effect of the foil, a small cut-out can be made in the foil at the position of the light source. To provide sufficient masking of the light source position, it is preferable to provide the cut-out at a minimum distance of at least 3 millimetres from the light source, preferably, at least 5 millimetres, more preferably at least 10 millimetres, e.g. 12 millimetres.

Advantageously, the present configuration may be applied for example in a light therapy device. Such a device is typically configured for providing a relatively high light intensity, e.g. more than 5,000 LUX at a distance of 20 centimetres from the front face of the light guide plate, or even higher, e.g. more than 7,000 LUX at said position. It will be appreciated that the advantages achieved by edge masking and by diminishing visible light spots, can improve the overall product appearance and eye comfort of the device.

In a second aspect, the present disclosure provides a method of masking an edge transition of an edge structure in a lighting device. The method comprises providing a light source to generate light. The light is emitted from a front side of the lighting device. The edge structure forms an outer circumference of a light window through which the light is transmitted towards the front side. The edge structure provides the transmitted light with said edge transition along the circumference of the edge structure. The method further comprises providing a patterned layer comprising a gradient edge pattern arranged with respect to the circumference of the edge structure to provide the transmitted light with a second edge transition. The gradient edge pattern superimposes the second edge transition on to the first edge transition. The method further comprises providing a diffuser between the front side and the patterned layer. The diffuser scatters the light of the second edge transition to provide the light emitted from the front side with a third edge transition. It will be appreciated that the method can be applied in a device as described herein. Also other applications may be envisaged.

BRIEF DESCRIPTION OF THE DRAWINGS

These and other features, aspects, and advantages of the apparatus, systems and methods of the present disclosure will become better understood from the following description, appended claims, and accompanying drawings, wherein:

DESCRIPTION OF EMBODIMENTS

Unless otherwise defined, all terms (including technical and scientific terms) used herein have the same meaning as commonly understood by one of ordinary skill in the art to which this invention belongs as read in the context of the description and drawings. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some instances, detailed descriptions of well-known devices and methods may be omitted so as not to obscure the description of the present systems and methods. Terminology used for describing particular embodiments is not intended to be limiting the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise it will be understood that when a connection between structures or components is described, this connection may be established directly or through intermediate structures or components unless specified otherwise. All publications, patent applications, patents, and other references mentioned herein are incorporated by reference in their entirety. In case of conflict, the present specification, including definitions, will control.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. The description of the exemplary embodiments is intended to be read in connection with the accompanying drawings, which are to be considered part of the entire written description. In the drawings, the absolute and relative sizes of systems, components, layers, and regions may be exaggerated for clarity. Embodiments may be described with reference to schematic and/or cross-sectional illustrations of possibly idealized embodiments and intermediate structures of the invention. In the description and the drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

Figure 1:
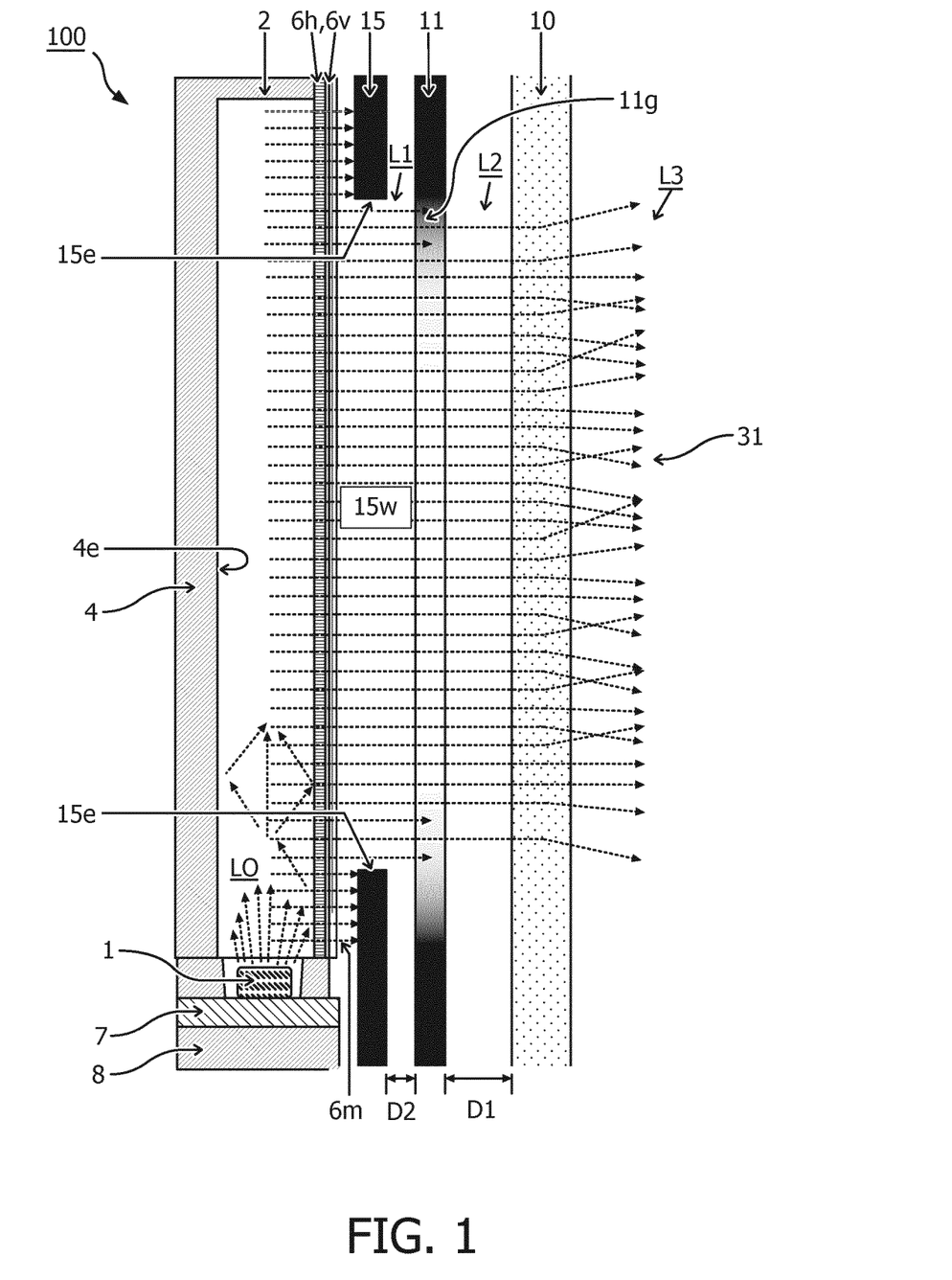
FIG. 1 shows a schematic cross-sectional view of an embodiment of a lighting device.

FIG. 1 shows a schematic cross-sectional view of an embodiment of a lighting device 100.

In one embodiment, the lighting device 100 comprises a light source 1 configured to emit light L0. It will be appreciated that the present disclosure provides particular benefit for light devices with a high-power light source 1. In one embodiment, the light source 1 is mounted on a circuit board 7. To prevent heat damage, preferably, the circuit board 7 is disposed between the side reflector 4 and a heat sink 8. For example, the heat sink plate 8 is configured to conduct heat produced by the light source 1 away from the circuit board 7. Alternatively, or in addition, the circuit board 7 may itself also function as a heat sink, e.g. a heat sink may be integrated in the circuit board 7. In one embodiment, the light source 1 comprises an emitter surface configured to emit light. The emitter surface may e.g. determine a direction in which most light is emitted. Preferably, the emitter surface used in the present disclosure is substantially flat to efficiently direct the light, although also other shapes are possible. For example, a dome shape may be used.

In one embodiment, the lighting device 100 comprises a light guide plate 2. The light guide plate 2 comprises a light entry surface 2a disposed at an edge of the light guide plate 2. Preferably, the light entry surface 2a is arranged to face the emitter surface 1a. The light entry surface 2a is configured to receive incident light from the emitter surface 1a and transmit at least part of the received incident light through the light entry surface 2a into an interior 2b of the light guide plate 2. The interior 2b of the light guide plate 2 typically consists of a solid transparent body, e.g. comprising plastic or glass. In a light guide plate 2, light is predominantly transported inside the plate, e.g. by internal reflections. In particular, in the embodiment shown, the light guide plate 2 comprises a front face 2c perpendicular to the light entry surface 2a, wherein the interior 2b of the light guide plate 2 is configured to guide the transmitted part of the incident light from the light entry surface 2a and distribute the light over the front face 2c to be emitted therefrom. It is noted that the light rays in the figure are drawn only schematically. In reality, the light may be distributed in different directions, e.g. by internal reflection inside the light guide plate. Also the light emitted from the front side of the plate can have a directional distribution.

In one embodiment, the light guide plate 2 is disposed at a distance from the emitter surface with an insulating gap therebetween. The insulating gap, also referred to as light chamber or cooling gap, may help to alleviate, i.e. lower/diminish, heat transfer from the light source 1 to the light guide plate 2. The insulating gap may e.g. comprise an air gap, or other gas, or even a vacuum. Also other transparent insulating material may be envisaged in the insulating gap. Alternatively to the gap, the light source 1 can also be placed against the light guide plate 2, e.g. with a flat-top LED. This may improve the light transfer efficiency but may also cause heating of the light guide plate.

In one embodiment, the lighting device comprises a front side 31 configured to emit the light from the lighting device 100. In the present embodiment, the front or light exit surface is formed by a diffusing transmitter 10. This can have the advantage of masking structures or patterns inside the device, also when the device is turned off, i.e. not producing light. Of course said definition of the "front" side 31 is arbitrary and is merely used to indicate a direction of the light in normal use. Alternatively, or in addition, light can be emitted from multiple sides of the device, e.g. also from the back or side. The principles for masking an edge transition can also be applied to multiple exit windows of light issuing from the device.

In one embodiment, the lighting device 100 comprises an edge structure 15 forming an outer circumference 15e of a light window 15w through which the light is transmitted towards the front side 31. In one embodiment, the edge structure 15 is disposed in a light path between the light source 1 and the front side 31. For example, the edge structure 15 can be formed by a component such as a clamp to hold the light guide plate 2 and/or other component layers. Alternatively, or in addition, the edge structure can also be formed by the edges of the light guide plate 2 itself. Alternatively, or in addition, the edge structure can also be formed by the edges of the light source itself. The edge structure 15, in use, casts a first edge transition L1, e.g. a sharp edge or shadow, on the emitted light behind the circumference 15e of the edge structure 15.

In one embodiment, the lighting device 100 comprises a patterned layer 11. In one embodiment, the patterned layer 11 is disposed between the edge structure 15 and the front side 31 of the device. Alternatively, although not preferably, the patterned layer can also be disposed between the edge structure 15 and the light source. In that case, the pattern L2 is produced before the light hits the edge. In one embodiment, the patterned layer 11 comprises a gradient edge pattern 11g configured to cast a second edge transition L2 on the transmitted light behind the gradient edge pattern 11g. In the shown embodiment, the gradient edge pattern 11g is configured with respect to the circumference 15e of the edge structure 15 to superimpose the second edge transition L2 on the transmitted light. In this way the smoothening by the first edge transition can be further smoothened by the second edge transition.

In one embodiment, the lighting device 100 comprises a diffuser 10 disposed between the front side 31 and the patterned layer 11. The diffuser 10 is configured to scatter the light from the second edge transition L2 to cast a third edge transition L3 on the light emitted from the front side 31. The scattering of the light from the second edge transition L2 of the gradient edge pattern 11g may cause further smoothening/masking of the visible edge.

In one embodiment, the diffuser 10 is disposed at a distance D1 from the patterned layer 11 with a spacing therebetween. For example, to improve blurring, the distance D1 is preferably more than 0 millimetre, more preferably more than 0.1 mm, even more preferably more than 1 mm, e.g. 1.9 mm. In one embodiment, the diffuser 10 is configured to increase the haze (spread) of light passing through the diffuser 10. For example, the haze or diffusion of the light may be increased by at least 10 percent as a result of passing through the diffuser 10. In one embodiment, the diffuser 10 has a thickness of at least 1 millimetre, e.g. at least 2 millimetres. In one embodiment, the diffuser 10 forms the front side 31 of the lighting device 100. Alternatively, other components are placed in front. In another embodiment (not shown), a gradient pattern is printed directly on the backside of the diffuser, i.e. D1=0 mm.

In one embodiment, the lighting device 100 comprises a light guide plate 2 disposed in a light path between the light source 1 and the edge structure 15. For example, the light guide plate 2 is configured to emit the light from the light source 1 towards the front side 31 of the lighting device 100. In one embodiment, the lighting device 100 comprises one or more brightness enhancement foils 6v,6h. The foils 6v,6h are preferably applied against the front face of the light guide plate 2 to at least partially collimate the outgoing light. Optionally, a foil 6v may comprise a cut-out, which will be discussed later with reference to FIG. 7.

It will be appreciated that the figure also illustrates a more general principle of masking an edge transition L1 of transmitted light of an edge structure 15 in a lighting device 100. In one embodiment, the method comprises providing a front side 31 to emit the light from the lighting device 10. For example, an edge structure 15 forms an outer circumference 15e of a light window 15w through which the light is transmitted towards the front side 31. For example, the edge structure 15 casts the edge transition L1 on the transmitted light behind the circumference 15e of the edge structure 15. In one embodiment, the method comprises providing a patterned layer 11 between the edge structure 15 and the front side 31 of the device. The patterned layer 11 comprises a gradient edge pattern 11g to cast a second edge transition L2 on the transmitted light behind the gradient edge pattern 11g. The gradient edge pattern 11g smoothens the first edge transition L1 by superimposing the second edge transition L2 on the transmitted light. In one embodiment, the method comprises providing a diffuser 10 between the front side 31 and the patterned layer 11, wherein the diffuser 10 scatters the light from the second edge transition L2 to cast a third edge transition L3 on the light emitted from the front side 31 to smoothen the second edge transition L2 of the gradient edge pattern 11g by scattering the light.

Figure 2A:
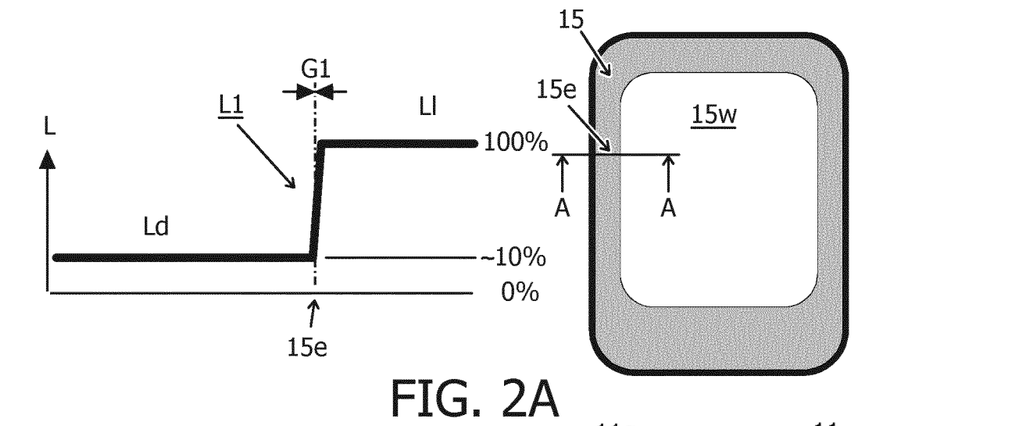
FIGS. 2A-2C show, on the right hand side, various layers of a lighting device, and, on the left hand side, schematic graphs of luminosity at the edge.
Figure 2B:
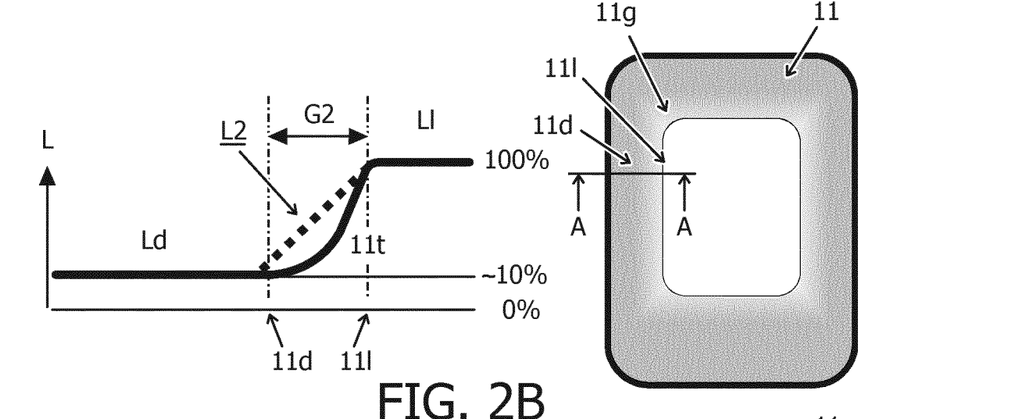
Figure 2C:
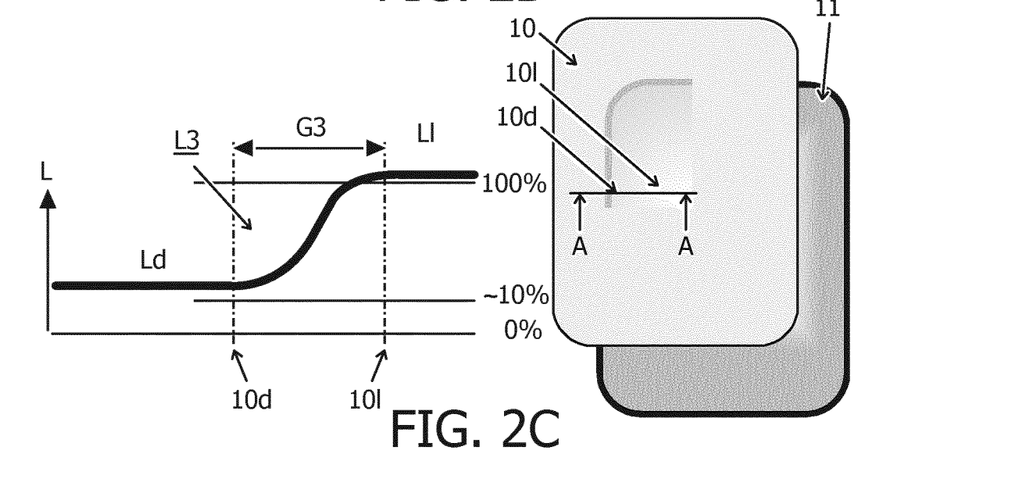

FIGS. 2A-2C show, on the right hand side, various layers of a lighting device, and, on the left hand side, schematic graphs of luminosity "L" at the edge across the distance indicated with arrows A-A. Luminosity can e.g. be measured in units of Candela per square metre (cd/m2).

FIG. 2A shows on the left side an example graph of luminosity L at the circumference edge 15 of an edge structure 15 shown on the right side, i.e. without edge masking. Because there is no gradient edge, the width G1 of the transition from maximum luminosity L1 to minimum luminosity Ld can be practically zero. Luminosity Ll at the light window 15w within the circumference 15e is set at 100%, i.e. full luminosity. In theory, e.g. a black foil with no gradient transition may produce a maximum-contrast edge with minimum edge hiding. The black foil may absorb all the environmental light and allow generated light to pass only through the opening. To reduce edge contrast, e.g. white foil can be used. The white foil may e.g. reflect an amount of environmental light while allowing the generated light to pass only through the opening e.g. to hide the inside structure of the device. As a result, contrast on the edge can be reduced by minimizing the absolute step in brightness difference between foil surface (Ll) and panel brightness (Ld). However, the result will depend on the environmental lighting conditions. In absolute darkness the effect will be 0%. In very bright environmental conditions and reduced brightness of the light panel it might be 100%. In practice this effect is expected to raise the luminosity Ld of the "dark" part of the device to about 10% of the full luminosity Ll. It is noted that the inside of the foil can still be made light-tight in order to hide artifacts caused by light leakage in the interior of the device. In practice this can be performed e.g. by means of black paint on the inside.

FIG. 2B is similar to FIG. 2A, except that a patterned layer 11 is introduced in front of the edge structure. Also in this embodiment, an amount of environmental light can be reflected, e.g. by white foil. In addition, emitted light is partially passed through a gradient edge, depending on the density gradient.

In one embodiment, the patterned layer 11 comprises a first area having a relatively low transparency 11d and a second area having a relatively high transparency 11l. In one embodiment, the patterned layer 11 is configured to determine the light transmission through the patterned layer 11, when the lighting device 100 is in use. In one embodiment, a luminosity Ld of the transmitted light through the first area having a relatively low transparency 11d is less than 30% of a luminosity Ll through the second area having a relatively high transparency 11l. In one embodiment, the gradient edge pattern 11g is configured to provide a luminosity transition gradient 11t of transmitted light therebetween. In one embodiment, a gradient edge width G2 between the first area having a relatively low transparency 11d and the second area having a relatively high transparency 11l is in a range of 3 to 15 millimetres. In one embodiment, a surface of the gradient edge width is between 3-30% of a total surface.

FIG. 2C is similar to FIG. 2B, except that a diffuser 10 is introduced in front of the patterned layer 11 (offset and partially overlapping to illustrate the effect). The diffuser 10 can have one or more of the following effects: masking details of the main light (e.g. dot pattern on the light guide plate), masking the pattern of the gradient edge, softening a transition from dark to light. In addition, reflection of environmental light on the diffuser may reduce a relative brightness step by raising brightness uniformly over the device. The degree may depend on the reflection characteristics of the diffuser. Alternatively, or in addition, by enlarging the distance from the diffuser to the gradient foil (set back), the hiding effect and blurring effect of the transition can be increased. The distance may be limited by the design freedom. Alternatively, or in addition, by reducing the translucency of the diffusing material (making it more milky), the hiding effect and blurring effect of the transition can be increased. As increased translucency normally entails increased light absorption, the translucency may be limited by the available amount of light that can be used to increase the gradient.

The width of the gradient transition may depend on several parameters. For example, the requested (perceptive) seamlessness of the light image, wherein seamlessness is defined e.g. by brightness transition/mm (rises and/or drops). Because the gradient may also absorb some light, the width can also be determined by the amount of light available to perform the transition. In practice, the surface of the gradient part is preferably chosen in the range of 3-30%.

A transition of the gradient edge may depend on several parameters. For example, because a white top layer already reflects environmental light, the theoretical gradient difference may be equal to the percentage of light already reflected. In practice, the density of the pattern on the outside may be around 10%. As the eye is not very sensitive to very small brightness differences, in practice the relative opening of the pattern on the inner side (light side) can be around 80%. For example, the kind of transition from minimum to maximum brightness may be optional, as the eye is not able to determine these differences. In one embodiment, the transition is logarithmic. In one embodiment, the transition ranges from 10% to 80%. A linear transition is also possible (see dotted line in FIG. 2B). Also other transitions are possible.

Figure 3A:
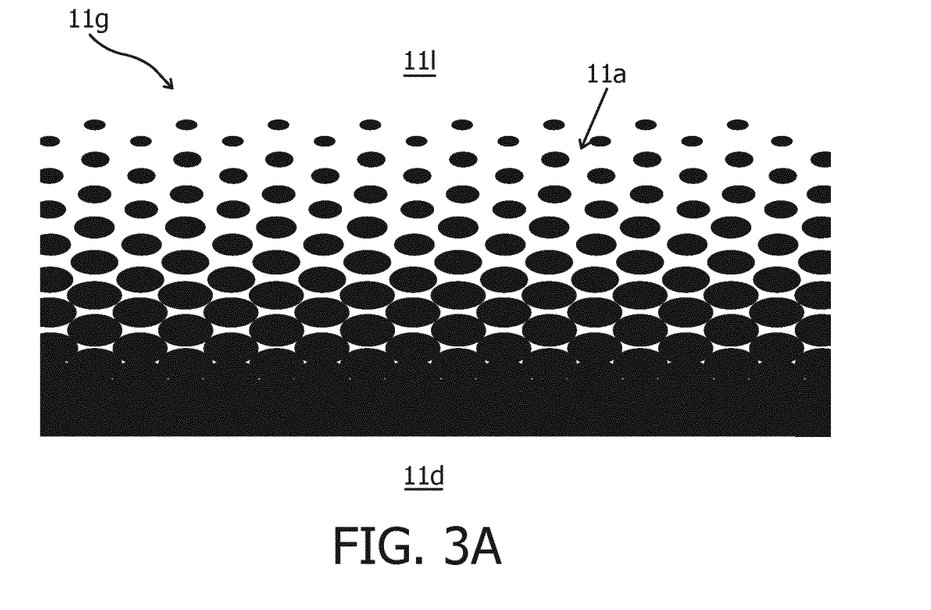
FIG. 3A shows an example gradient edge pattern.

FIG. 3A shows an example gradient edge pattern 11g. In one embodiment, the gradient edge pattern 11g comprises a distribution of reflecting and/or translucent and/or absorbing FIG. 11a. In one embodiment, the density of the distribution and/or size of the figures and/or the transparency of the figures varies across the gradient edge pattern 11g between a first area having a relatively low transparency 11d, a low density and/or small size, and a second area having a relatively high transparency 11l, a high density and/or large size. For example, the gradient edge can be produced by dots printed on a foil. The gradient can e.g. be realized by one or more of: changing the dot size, changing the dot density (e.g. with same dot size), or a combination thereof. As a result, the brightness drop/mm of the transition on the edge can be reduced by the white surface of the foil and/or a gradient width G2 (width of the gradient zone) from non-transparent to fully transparent.

The colour of the pattern is preferably white. The white surface helps to reflect environmental light. Because white lacquers are typically translucent (e.g. black is light-tight), the white dots prevent hard transitions from the light from the backside. Preferably, the size of the dot should be invisible. Accordingly, the size of the dot may be chosen in such a way that the dot is not visible by the naked eye. This can depend on resolution and distance to the user. A preferred pattern is optimized for a distance of 10-100 cm. The resolution of the human eye can be found in literature and is around 0.3 arc minutes. It is noted that there may be a strong interaction with the applied diffuser on top of the device. In an embodiment, the dot diameter varies between 0-2 mm. The minimum dot size may be determined by the applied production method, e.g. silk screen printing. Alternatively, or in addition to a pattern of dots, also other variations are possible for achieving a gradient effect. For example, in one embodiment the gradient edge pattern comprises a collection of concentric lines wherein the spacing and/or transparency of the lines vary over a gradient distance of the pattern.

Figure 3B:
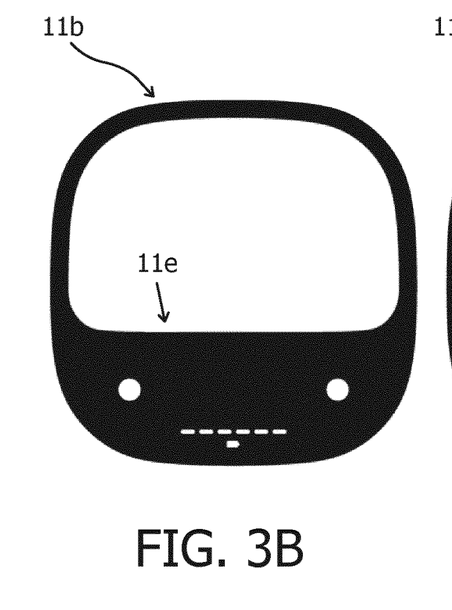
FIGS. 3B and 3C show examples of sub-layers of an embodiment of a patterned layer.
Figure 3C:
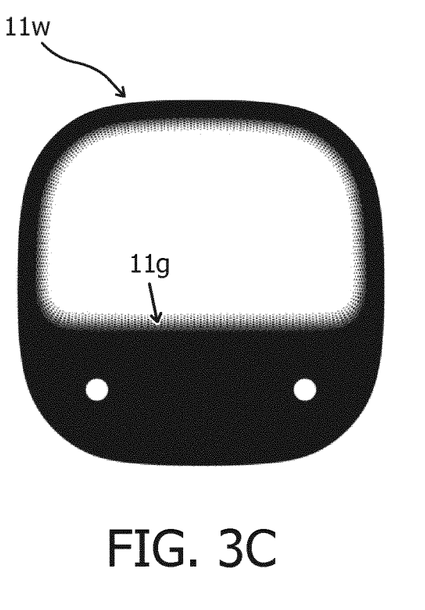

FIGS. 3B and 3C show example sub-layers of an embodiment of a patterned layer. FIG. 3B shows an example of a light-blocking layer 11b preventing light leakage from the interior of the device. FIG. 3C shows an example gradient pattern layer 11w for providing a gradient transition. Both layers are displayed in a black colour to show the pattern, but the actual colour may vary. In one embodiment, the patterned layer 11 comprises a first patterned material 11b configured to absorb and/or reflect at least 70 percent of the light L0 from the light source 1. For example, a black material can be used for this. In another or further embodiment, the patterned layer 11 comprises a second patterned material 11w covering the first patterned material 11b on the front side 31 of the lighting device 100, wherein the second patterned material 11w is configured to form the gradient edge pattern 11g. Although shown in black on the right hand side of this figure, in one embodiment, the second patterned material 11w has a colour matching that of the front side 31 of the lighting device 100 (e.g. the colour of the diffuser 10, e.g. white) to hide the second patterned material 11w from view on the front side 31 (see also FIGS. 4A-4C). The pattern does not need to be fully light-blocking to achieve the desired effect. The layer may be translucent (with a sufficient contrast ratio) to show the desired effect.

Figure 4A:
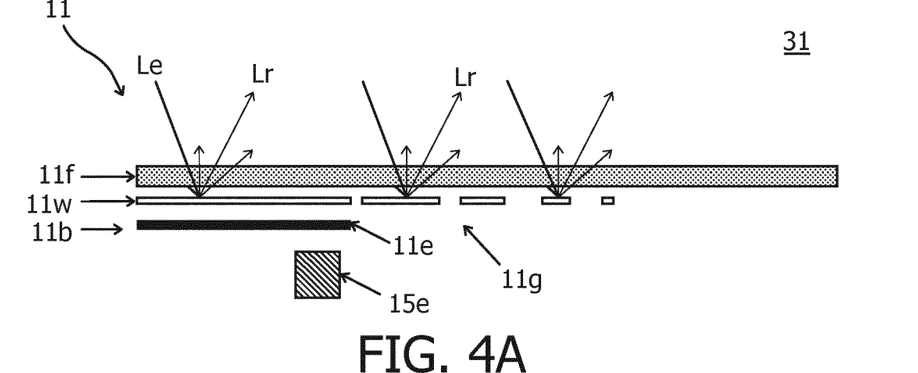
FIGS. 4A-4C show schematic cross-sectional views of a patterned layer.
Figure 4B:
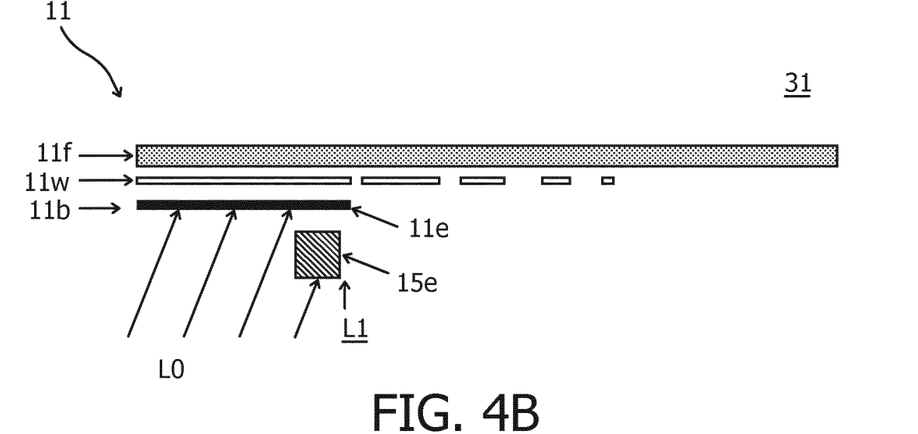
Figure 4C:
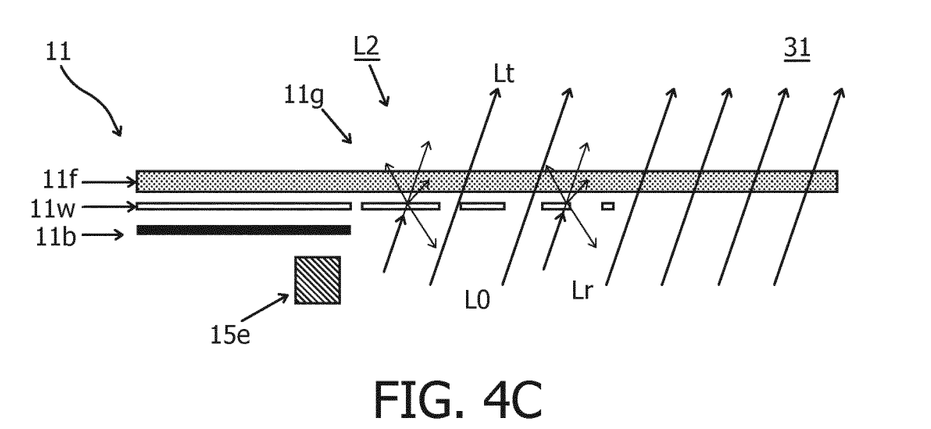

FIGS. 4A-4C show schematic cross-sectional views of a patterned layer. FIG. 4A illustrates diffuse reflection Lr of environmental light Le. FIG. 4B illustrates absorption of light leakage in a device by a black or other light-tight layer 11w. FIG. 4C illustrates transmission Lt of main light L0 through gradient edge 11g and reflection Lr of main light L0 by gradient edge 11g. In practice, the processes illustrated by FIGS. 4A-4C may occur in combination with one another. In one embodiment, the patterned layer 11 comprises a transparent foil 11f. In one embodiment, the gradient edge pattern 11g is printed on the backside of the foil, opposite the front side 31 of the lighting device 100. The gradient edge pattern 11g may e.g. by comprised in a second patterned material 11w, as described with reference to FIG. 3B. In addition, the figures illustrate a first patterned material 11b, in this case on top of the second patterned material 11w, opposite the front side 31 of the device.

Figure 5:
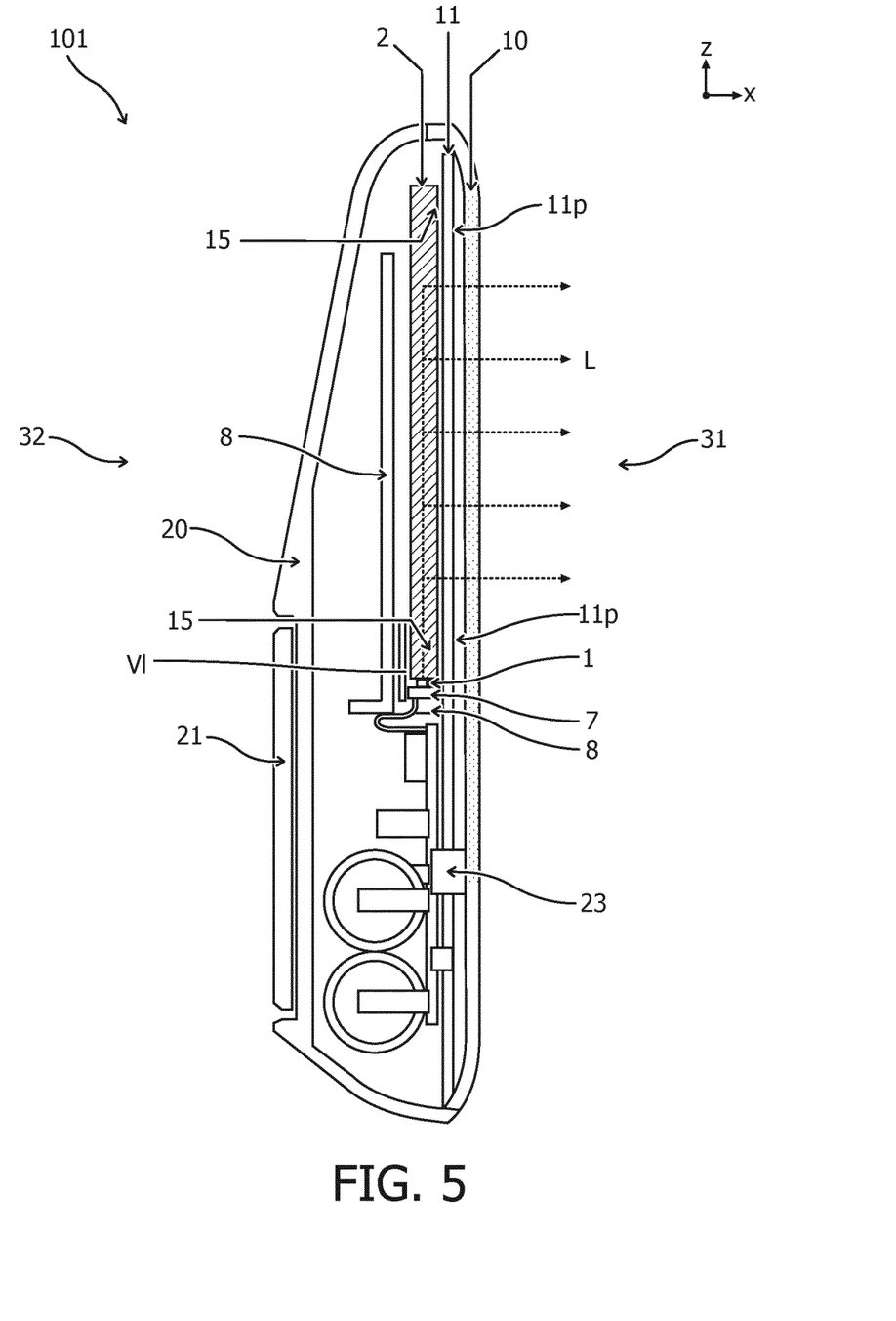
FIG. 5 shows a schematic cross-sectional side view of an embodiment of a light therapy device.

FIG. 5 shows a schematic cross-sectional side view of an embodiment of a light therapy device 101. In one embodiment, the lighting device 100 of FIG. 1 forms, or is integrated into, the light therapy device 101. A light therapy device may e.g. be characterized by its intended use. In one embodiment, a lighting device 100 as described herein is configured to provide a light intensity of more than 5000 LUX at a distance of 20 centimetres from the front side 31 of the lighting device 100. The light intensity is e.g. provided over a certain area in front of the device, e.g. an area of more than 10 square centimetres, preferably more than 50 square centimetres, or even more, e.g. 100 square centimetres. Another parameter of a light therapy device may be its wavelength or bandwidth, e.g. blue and/or white light. For certain light therapy applications, it has been found that light in a particular frequency range can be more effective than white light. For example, the total light intensity necessary for achieving a desired effect can be lower when using only blue light. In one embodiment, a lighting device as described herein is configured to provide light in a wavelength range between 460-490 nanometres. In a further embodiment, a lighting device as described herein is configured to provide light in the said wavelength range between 460-490 nanometres, wherein the light intensity is more than 100 LUX (preferably more than 200 LUX) at a distance of 50 centimetres from the front side 31 of the lighting device 100. It is noted that LUX is a photometric measure of the intensity, as perceived by the human eye, i.e. power at each wavelength weighted according to the luminosity function.

In one embodiment, the device comprises a heat sink plate 8, which may dissipate excess heat, e.g. by radiation from a back side 20 of the device. In one embodiment, the device comprises a control means 23 integrated, e.g. on the front side of the device or elsewhere on the device, e.g. on the back side 20. In one embodiment, the device comprises a support foot 21, e.g. for placing the device on a table top. Of course, components described herein can be omitted and/or other components added without sacrificing an intended functionality of the device.

Figure 6A:
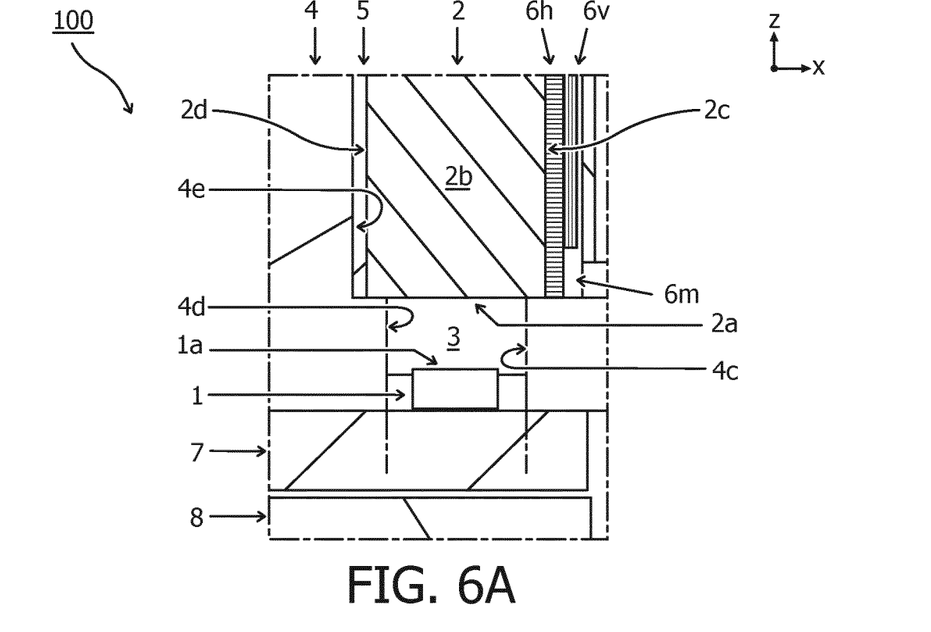
FIG. 6A shows a detailed cross-sectional side view around a light source.

FIG. 6A shows a detailed cross-sectional side view around a light source, e.g. the area "VI" indicated in FIG. 5, or another lighting device.

In one embodiment, the light guide plate 2 comprises a light entry surface 2a disposed at an edge of the light guide plate 2 and facing an emitter surface 1a of the light source 1, wherein the light entry surface 2a is configured to receive incident light L0 from the emitter surface 1a and to transmit at least part of the received incident light L0 through the light entry surface 2a into an interior 2b of the light guide plate 2; wherein the light guide plate 2 comprises a front face 2c perpendicular to the light entry surface 2a, wherein the interior 2b of the light guide plate 2 is configured to guide the transmitted part of the incident light L0 from the light entry surface 2a and distribute the light over the front face 2c to be emitted therefrom towards the front side 31 of the lighting device 100.

In one embodiment, the light guide plate 2 is disposed at a distance from the emitter surface 1a with an air gap 3 therebetween. The air gap 3, also referred to as light chamber, may help to alleviate, i.e. lower/diminish, local heating of the light guide plate 2 by the light source 1. The air gap 3 may e.g. comprise air, or other gas, or even a vacuum. Also other transparent material may be envisaged in the air gap 3. Alternatively, e.g. if heating is not relevant, the light source can be placed in direct contact with the light guide plate 2. To improve efficiency, the sides 4c, 4d may comprise a reflective material.

In one embodiment, a reflecting structure 4 extends so as to cover also a back face 2d of the light guide plate 2. In particular, in the embodiment the reflecting body 4 comprises a back reflector surface 4e configured to reflect light exiting the back face 2d of the light guide plate 2. By having multiple reflecting surfaces integrated in a single reflector body, the construction may be simplified. Alternatively, it may be envisaged that each of the reflecting surfaces, 4c, 4d, 4e is part of separate reflecting bodies.

In one embodiment, a diffusor reflector foil 5 is arranged between the back surface 4e of the reflector and the back face 2d of the light guide plate 2. The diffusor reflector 5 is configured not only for reflecting but also for diffusing an angle of the reflected light. In this way, a more homogeneous light distribution may be effected and the efficacy of the brightness enhancement foils 6v and 6h is improved. Alternatively, or in addition, also the back surface 4e of the reflector may have a diffusing effect on the reflected light angle. For example, the back surface 4e of the reflector and/or the diffusor reflector 5 may comprise a roughened surface to scatter the reflected light.

In one embodiment, brightness enhancement foils 6v,6h are arranged at a front face 2c of the light guide plate 2. For example, in one embodiment, the foil 6v is configured to collimate outgoing light in a horizontal direction while the foil 6h is configured to collimate outgoing light in a vertical direction. The collimation may e.g. be effected by ridges on the foil. A combined effect of the foils may be that the brightness of the light is enhanced in particular directly in front of the output face of the device. Of course, the foils are optional, and may be omitted or replaced by other collimating structures. In the present embodiment, one of the foils 6v comprises a cut-out 6m near the light source 1, which will be discussed in FIG. 7 below.

Figure 6B:
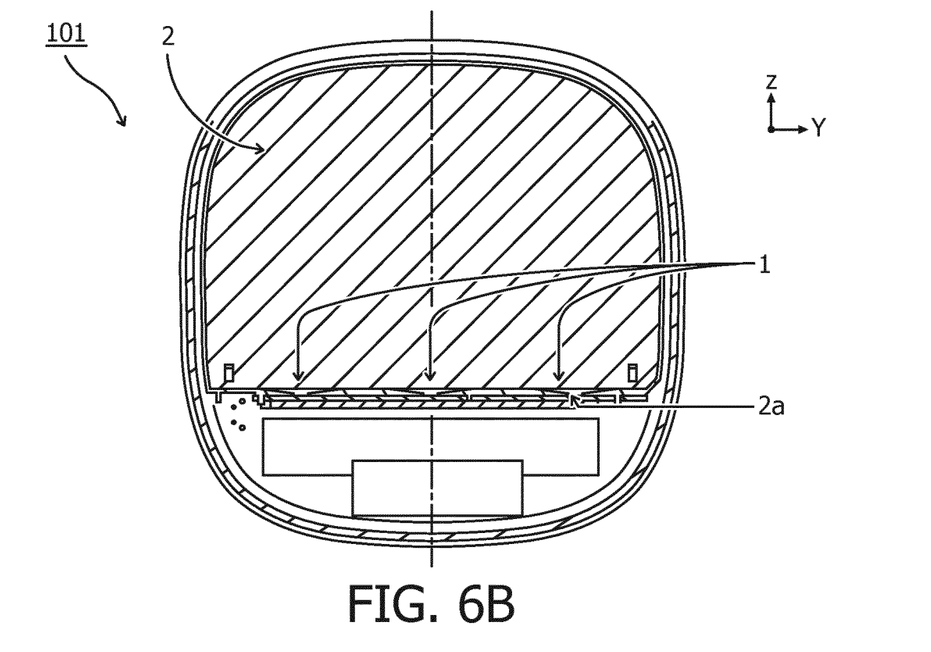
FIG. 6B shows a schematic cross-sectional front view of an embodiment of a light therapy device.

FIG. 6B shows a schematic cross-sectional front view of an embodiment of a light therapy device. The view illustrates, for example, the extent of the light guide plate 2 and the placement of the light sources 1 against a light entry surface 2a of the plate 2. While the light sources are shown to be placed only at the bottom, alternatively, or in addition, one or more light sources 1 are placed at different edges of the light guide plate 2. Light sources can also be placed elsewhere. And the use of a light guide plate 2 is optional.

Figure 7A:
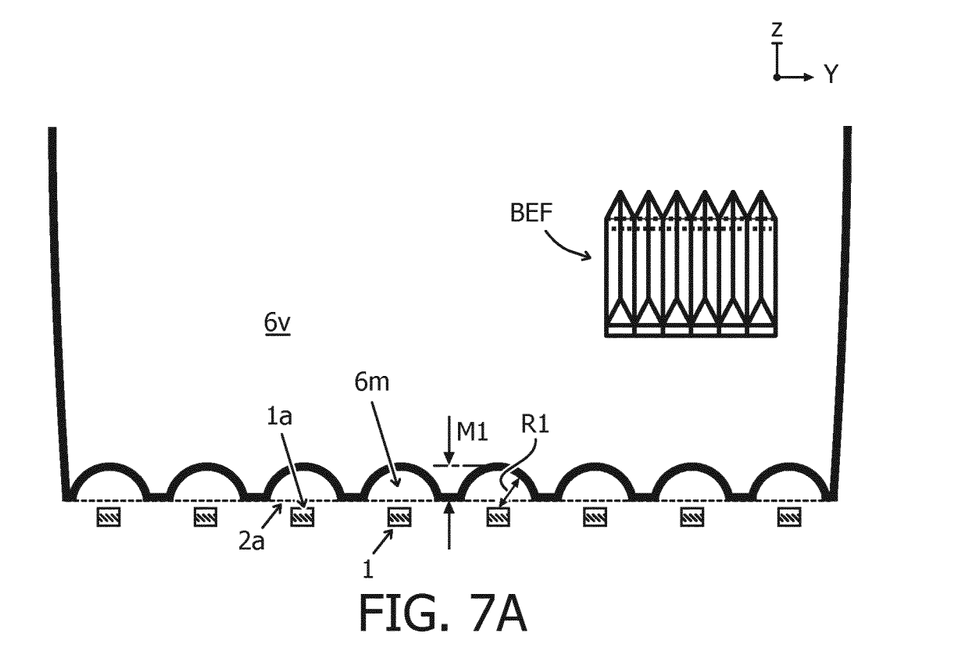
FIG. 7A shows a schematic embodiment of a brightness enhancement foil.

FIG. 7A shows a schematic embodiment of a brightness enhancement foil 6v, e.g. as discussed herein. In one embodiment, the brightness enhancement foil 6v comprises a ridged structure of vertical ridges disposed in a Z direction along the front face 2c perpendicularly to the light entry surface 2a. The ridged structure (e.g. schematically illustrated by the insert "BEF" in the figure) is e.g. configured to collimate transmitted light in a horizontal direction Y. In one embodiment, an edge of the brightness enhancement foil 6v, on the side of the light entry surface 2a, comprises a cut-out 6m.

In one embodiment, a second brightness enhancement foil 6h is provided, e.g. as shown in FIG. 6A. The second brightness enhancement foil 6h comprises a ridged structure of horizontal ridges disposed in a Y direction along the front face 2c perpendicularly to the light entry surface 2a. The ridged structure (not shown here) is e.g. configured to collimate transmitted light in a vertical direction Z. In one embodiment, the first brightness enhancement foil 6v comprises the cut-out 6m while the second brightness enhancement foil 6h does not, i.e. it comprises a straight edge. It has been found that for the second brightness enhancement foil 6h, the occurrence of light lanes is less prominent, e.g. because of the differing directions of the ridges. In one embodiment, the second brightness enhancement foil 6h is disposed between the first brightness enhancement foil 6v and the light guide plate 2 to further reduce the effect of the light lanes (see e.g. FIG. 6A).

In one embodiment, the cut-out 6m is disposed at a minimum (radial) distance R1 from the emitter surface 1a of a light source For example, in one embodiment, the distance, viewed perpendicularly to the front face 2c, is at least 5 millimetres, e.g. 12 millimetres. The cut-out is preferably circular. The centre is not necessarily at the edge of the foil, but may e.g. be at the emitter surface 1a or the light entry surface 2a. In one embodiment, the cut-out 6m extends over a distance Ml of more than 5 millimetres into the foil, e.g. 8 or 9 millimetres.

Figure 7B:
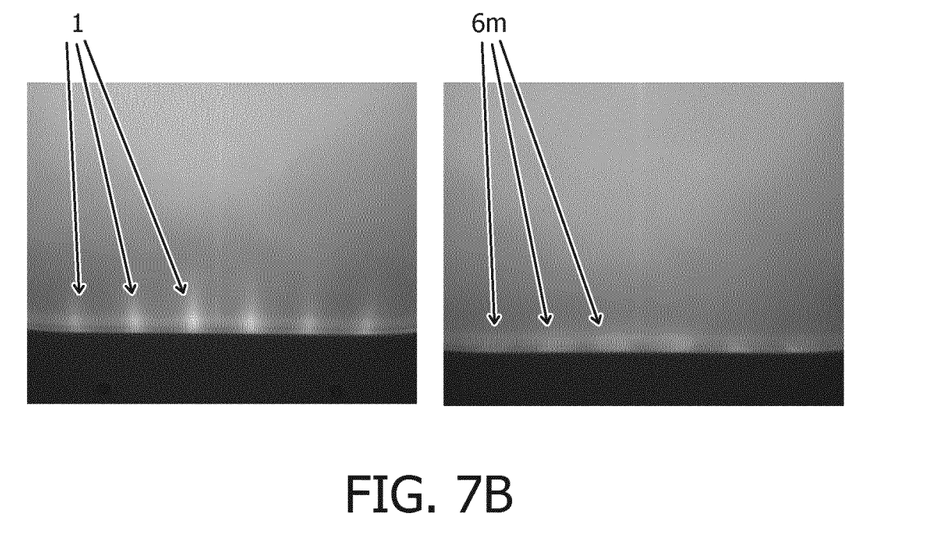
FIG. 7B shows an effect of masking visible light lanes.

FIG. 7B shows an effect of the cut-outs 6m on the visual appearance from the front side of the device. On the left hand side, the cut-out is not applied to the foil and the light lanes are clearly visible at the bottom of the display near the light sources 1. On the right hand side, it can be seen that the light lanes are less visible/better masked. It will be appreciated that the application of a cut-out in the brightness enhancement foil 6v to mask light lanes of nearby light sources is not limited to the present devices. For example, it can be applied in other situations where a brightness enhancement foil is placed against a light guiding structure receiving light from an edge of the structure. For example, the principle can be applied also in television or other display screens. In such applications, e.g. one or more of the diffuser 10 and/or patterned layer 11 may be omitted.

Figure 8:
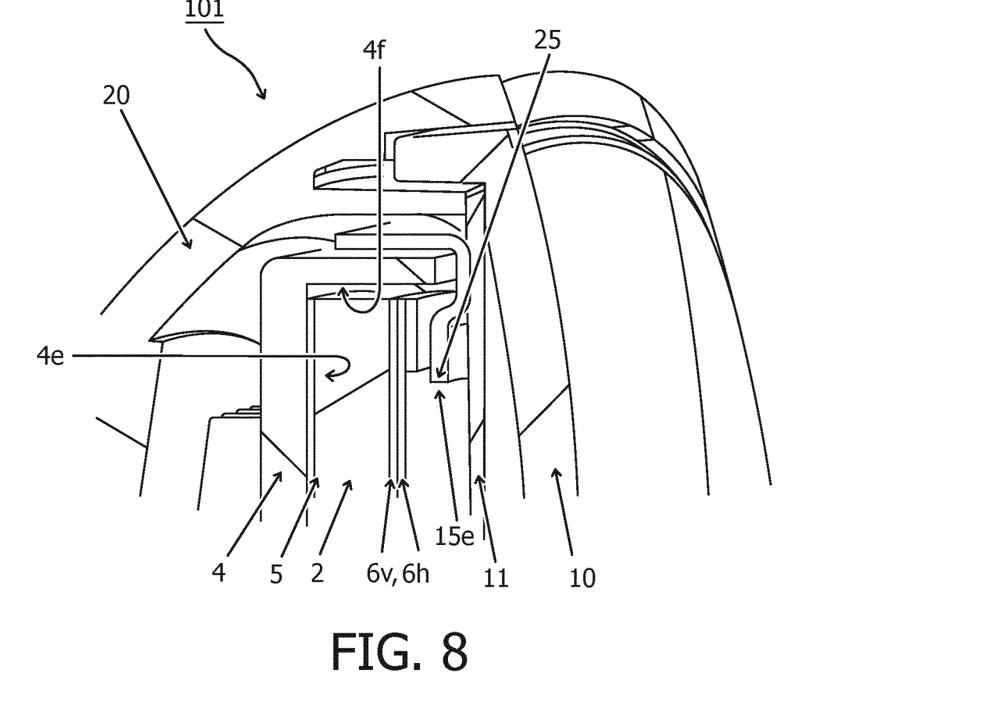
FIG. 8 shows a cross sectional side view of a top part of a light therapy device.

FIG. 8 shows a cross sectional side view (mostly XZ) of a top part of a light therapy device 100. In the figure, various components are visible that may be part of an embodiment of a light therapy device 100. Other embodiments may comprise additional or fewer components and/or in different arrangements and shapes.

In the present view shown in FIG. 8, the following components are indicated (from front to back): a front diffusing transmitter 10, a patterned foil 11, brightness enhancement foils 6h and 6v, a light guide 2, a diffusor reflector foil 5, a reflector body 4, and a backside 20 of the device. In the shown embodiment, the reflector body encloses the light guide plate 2 on all sides except the front face side and at the positions of the light sources, where the air gap 3 is provided. In one embodiment, a clamping structure 25 is arranged for holding one or more of the components 4,5,2,6v,6h. In one embodiment, an edge of the clamping structure 25 forms the circumference 15e of the edge structure casting light with an edge onto the patterned layer 11.

Figure 9A:
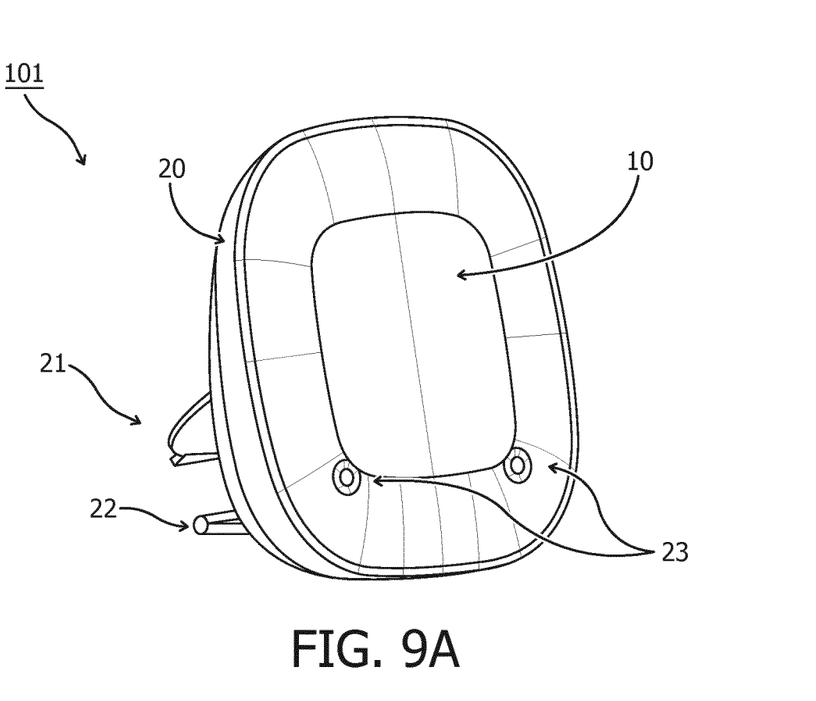
FIGS. 9A and 9B show perspective views of embodiments of light therapy devices.
Figure 9B:
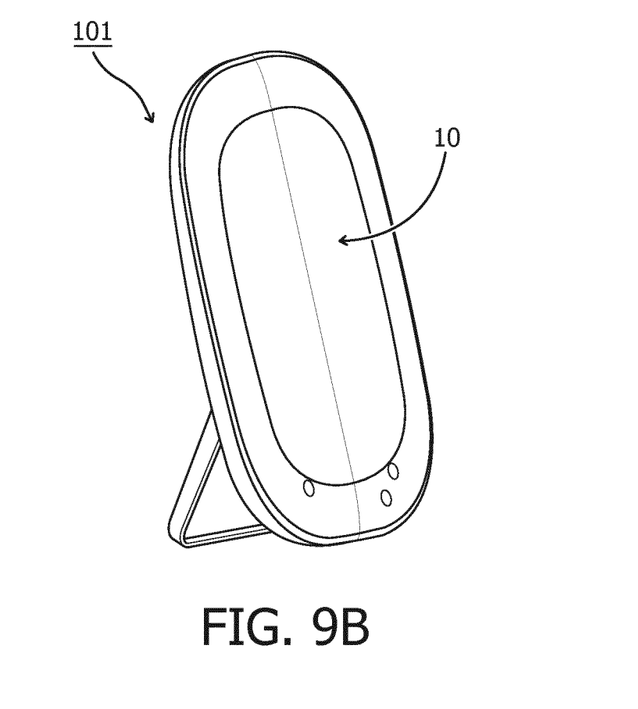

FIGS. 9A and 9B show perspective views of embodiments of various light therapy devices. FIG. 9A shows an example high-end device with blue LED light sources. The device 100 in this embodiment comprises a front 10, a back 20, a support foot 21, and a power cord. Of course also other configurations are possible. FIG. 9B shows another example of a light therapy device, which, in this case, is operable with white light LEDs. This device may e.g. have a larger front surface. Of course many different design variations are possible providing an equivalent function. In general, it is preferred that a light therapy device be capable of delivering a certain dose of light with considerable eye comfort. To be an effective therapy, preferably, at least part of the light is in the blue part of the spectrum. In one embodiment, a lighting device is configured for providing a light intensity of more than 5000 LUX at a distance of 20 centimetres from the front face 10 of the device. For some applications, even higher intensities may be desired, e.g. more than 10,000 LUX at said distance.

For the purpose of clarity and a concise description, features are described herein as part of the same or separate embodiments, however, it will be appreciated that the scope of the invention may include embodiments having combinations of all or some of the features described. For example, while embodiments were shown of a lighting device with certain arrangements or combinations of components, also alternative ways may be envisaged by those skilled in the art having the benefit of the present disclosure for achieving a similar function and result. For example, optical and/or electrical components may be combined or split up into one or more alternative components. The various elements of the embodiments as discussed and shown offer certain advantages, such as masking an edge of a display. Of course, it is to be appreciated that any one of the above embodiments or processes may be combined with one or more other embodiments or processes to provide even further improvements in finding and matching designs and advantages. It is appreciated that this disclosure offers particular advantages to light therapy devices, and in general can be applied for any application wherein light sources are used to provide an illuminated surface, e.g. in combination with light guiding plates.

While the present systems and methods have been described in particular detail with reference to specific exemplary embodiments thereof, it should also be appreciated that numerous modifications and alternative embodiments may be devised by those of ordinary skill in the art without departing from the scope of the present disclosure. For example, embodiments wherein devices or systems are disclosed which are to be arranged and/or constructed for performing a specified method or function inherently disclose the method or function as such and/or in combination with other disclosed embodiments of methods or systems. Furthermore, embodiments of methods are considered to inherently disclose their implementation in respective hardware, where possible, in combination with other disclosed embodiments of methods or systems. Furthermore, methods that can be embodied as program instructions, e.g. on a non-transient computer-readable storage medium, are considered to be inherently disclosed as such an embodiment.

Finally, the above-discussion is intended to be merely illustrative of the present systems and/or methods and should not be construed as limiting the appended claims to any particular embodiment or group of embodiments. The specification and drawings are accordingly to be regarded in an illustrative manner and are not intended to limit the scope of the appended claims. In interpreting the appended claims, it should be understood that the word "comprising" does not exclude the presence of elements or acts other than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. The mere fact that certain measures are recited in mutually different claims does not indicate that a combination of these measures cannot be used to advantage. In particular, all effective combinations of the claims are considered inherently disclosed.

The invention claimed is:

1. A lighting device comprising
a light source configured to generate light;
a front side configured to emit the light from the lighting device;
an edge structure forming an outer circumference of a light window through which the light is transmitted towards the front side; wherein the edge structure, in use, provides the transmitted light with a first edge transition along the circumference of the edge structure;
a patterned layer comprising a gradient edge pattern configured to provide the transmitted light with a second edge transition; wherein the gradient edge pattern is arranged with respect to the circumference of the edge structure to superimpose the second edge transition on the first edge transition;
a diffuser disposed between the front side and the patterned layer such that no portion of the diffuser is in contact with any portion of the patterned layer, wherein the diffuser is configured to scatter the light of the second edge transition to provide the light emitted from the front side with a third edge transition.

2. The lighting device according to claim 1, wherein the diffuser is disposed at a distance from the patterned layer with a spacing between the patterned layer and the diffuser, wherein the distance is more than 1 millimetre.

3. The lighting device according to claim 1, wherein the diffuser gives a haze ratio of transmitted light of at least 5 percent.

4. The lighting device according to claim 1, wherein the diffuser forms the front side of the lighting device.

5. The lighting device according to claim 1, wherein the edge structure is disposed in a light path between the light source and the front side.

6. The lighting device according to claim 1, wherein the patterned layer comprises a first area having a relatively low transparency and a second area having a relatively high transparency, wherein the gradient edge pattern is configured to provide a luminosity transition gradient of the transmitted light extending between the first area and the second area, wherein a gradient edge width between the first area and the second area is in a range of 3 to 15 millimetres.

7. The lighting device according to claim 1, wherein the patterned layer comprises
a first patterned material configured to absorb and/or reflect at least 90 percent of the light from the light source; and
a second patterned material covering the first patterned material from the front side of the lighting device, wherein the second patterned material is configured to form the gradient edge pattern.

8. The lighting device according to claim 7, wherein the second patterned material has a colour matching that of the front side of the lighting device to mask the second patterned material in the case of a view of the front side.

9. The lighting device according to claim 1, wherein the gradient edge pattern comprises a distribution of reflecting and/or translucent and/or absorbing figures, wherein a transparency of the figures and/or a density of the distribution and/or size of the figures varies across the gradient edge pattern between a first area having a relatively low transparency and a high density and/or large size, and a second area having a relatively high transparency and a low density and/or small size.

10. The lighting device according to claim 1, wherein the patterned layer comprises a transparent foil, wherein the gradient edge pattern is printed on a backside of the foil, opposite the front side of the lighting device.

11. The lighting device according to claim 1, comprising a light guide plate disposed in a light path between the light source and the edge structure, wherein the light guide plate is configured to emit the light of the light source towards the front side of the lighting device.

12. The lighting device according to claim 11, wherein the light guide plate comprises a light entry surface disposed at an edge of the light guide plate and facing an emitter surface of the light source, wherein the light entry surface is configured to receive incident light from the emitter surface and to transmit at least part of the received incident light through the light entry surface into an interior of the light guide plate; wherein the light guide plate comprises a front face perpendicular to the light entry surface, wherein the interior of the light guide plate is configured to guide the transmitted part of the incident light from the light entry surface and distribute the light over the front face to be emitted therefrom towards the front side of the lighting device.

13. The lighting device according to claim 12, comprising a brightness enhancement foil disposed against the front face of the light guide plate, wherein the brightness enhancement foil comprises a ridged structure (BEF) of vertical ridges disposed in a direction (Z) along the front face perpendicular to the light entry surface, wherein the ridged structure (BEF) is configured to collimate transmitted light in a horizontal direction (Y), wherein an edge of the brightness enhancement foil comprises, on a side of the light entry surface, a cut-out with a minimum distance from the emitter surface along a view perpendicular to the front face of at least 5 millimetres.

14. A light therapy device comprising the lighting device according to claim 1, wherein the lighting device is configured to provide a light intensity in a wavelength range between 460-490 nanometres of more than 200 LUX at a distance of 50 centimetres from the front side of the lighting device.

* * * * *